(12) United States Patent
Dudley

(10) Patent No.: US 7,960,553 B1
(45) Date of Patent: Jun. 14, 2011

(54) REAGENT FOR SYNTHESIS OF PARA-METHOXBENZYL (PMB) ETHERS AND ASSOCIATED METHODS

(75) Inventor: Gregory B. Dudley, Tallahassee, FL (US)

(73) Assignee: Florida State University Research Founation, Inc., Tallahassee, FL (US)

( * ) Notice: Subject to any disclaimer, the term of this patent is extended or adjusted under 35 U.S.C. 154(b) by 853 days.

(21) Appl. No.: 11/865,952

(22) Filed: Oct. 2, 2007

Related U.S. Application Data

(60) Provisional application No. 60/827,763, filed on Oct. 2, 2006, provisional application No. 60/862,121, filed on Oct. 19, 2006.

(51) Int. Cl.
*C07D 215/04* (2006.01)

(52) U.S. Cl. .................................................. 546/181
(58) Field of Classification Search ............... 546/181
See application file for complete search history.

(56) References Cited

U.S. PATENT DOCUMENTS 7,754,909 B1 * 7/2010 Dudley ..................... 558/27

* cited by examiner

*Primary Examiner* — Nizal S Chandrakumar
(74) *Attorney, Agent, or Firm* — Allen, Dyer, Doppelt, Milbrath & Gilchrist, P.A.

(57) ABSTRACT

A newly synthesized compound designated lepidine ether 2-(4-Methoxybenzyloxy)-4-methylquinoline reacts with methyl triflate in the presence of alcohols to generate a neutral organic salt that transfers the para-methoxybenzyl (PMB) protecting group onto alcohols in high yield and under mild conditions.

1 Claim, 4 Drawing Sheets

Equation (1)

Equation (2)

Equation (3)

REAGENT FOR SYNTHESIS OF PARA-METHOXBENZYL (PMB) ETHERS AND ASSOCIATED METHODS

RELATED APPLICATION

This application claims priority from provisional applications Ser. No. 60/827,763, which was filed on Oct. 2, 2006, and Ser. No. 60/862,121, which was filed on Oct. 19, 2006, both of which are incorporated herein by reference in their entirety.

FIELD OF THE INVENTION

The present invention relates to the field of organic chemistry and, more particularly, to the synthesis of para-Methoxybenzyl (PMB) ethers.

BACKGROUND OF THE INVENTION para-Methoxybenzyl (PMB) ethers are workhorse protecting groups in organic synthesis.[1] Like benzyl (Bn) ethers, PMB ethers withstand a wide range of reaction conditions, can be cleaved under mild conditions,[2] and are not subject to the unwanted migration between neighboring functional groups that is observed with ester, acetal, and silyl ether protecting groups. However, the formation of PMB ethers can be problematic. Common methods for the synthesis of PMB ethers-Williamson[3] and trichloroacetimidate[4] coupling reactions-require basic or acidic media that may not be compatible with complex systems.[5] Furthermore, neither PMB trichloroacetimidate (unstable to storage) nor PMB chloride (lachrymator) is especially convenient for routine usage.

SUMMARY OF THE INVENTION

With the foregoing in mind, the present invention advantageously provides a synthesis of versatile PMB ethers that should be widely applicable in synthetic chemistry.[8] The present PMB ethers are analogous to those we recently introduced, 2-benzyloxy-1-methylpyridinium triflate (compound 4),[6] a stable organic salt that provides benzyl ethers upon warming in the presence of alcohols (Equation 1).[7]

The present invention, thus, discloses a novel para-Methoxybenzyl ether having the formula of compound 1. Additionally, the invention includes a method of making compound 1, also designated 2-(4-methoxybenzyloxy)-4-methylquinoline or lepidine ether, the method consisting of a reaction according to Equation 2. Also included in the invention is a method of making various para-methoxybenzyl ethers according to formulas 3 as shown in Table 1 and FIG. 2, the method comprising addition of methyl triflate to reaction mixtures containing a neutral alcohol 2 non-reactive with methyl triflate, the lepidine ether according to compound 1, and an aromatic solvent under an inert gas. This method may be carried out with the aromatic solvent being trifluorotoluene or, optionally, toluene. Additionally, the method may include argon as the inert gas. In this method, the reaction mixture may optionally contain magnesium oxide or, optionally, potassium carbonate.

BRIEF DESCRIPTION OF THE DRAWINGS

Some of the features, advantages, and benefits of the present invention having been stated, others will become apparent as the description proceeds when taken in conjunction with the accompanying drawings, presented for solely for exemplary purposes and not with intent to limit the invention thereto, and in which.

DETAILED DESCRIPTION OF THE PREFERRED EMBODIMENT

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. Any publications, patent applications, patents, or other references mentioned herein are incorporated by reference in their entirety. In case of conflict, the present specification, including any definitions, will control. In addition, the materials, methods and examples given are illustrative in nature only and not intended to be limiting. Accordingly, this invention may, however, be embodied in many different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

Figure 1:
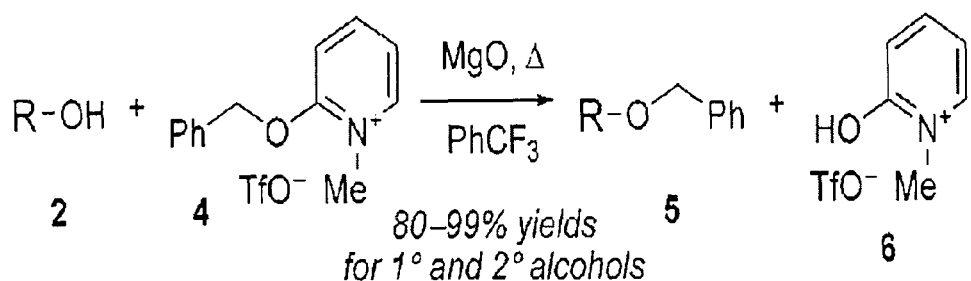
FIG. 1, along the top shows in Equation (1) a method of synthesizing 2-benzyloxy-1-methylpyridinium triflate, a compound employed in reactions according to embodiments of the present invention; along the bottom shows PMB salts.
Figure 1:
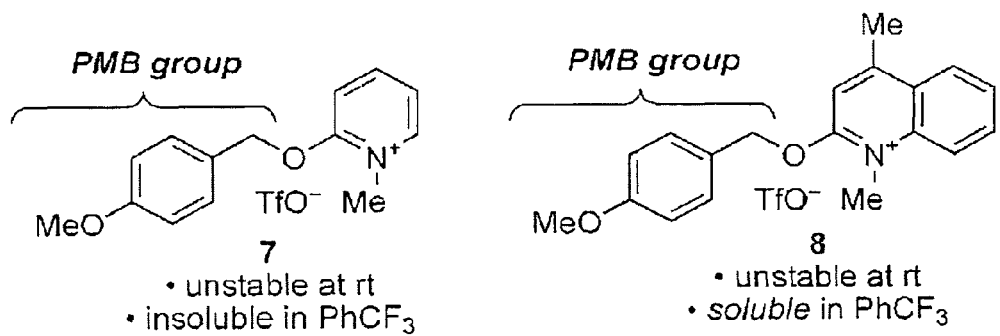
Figure 2:
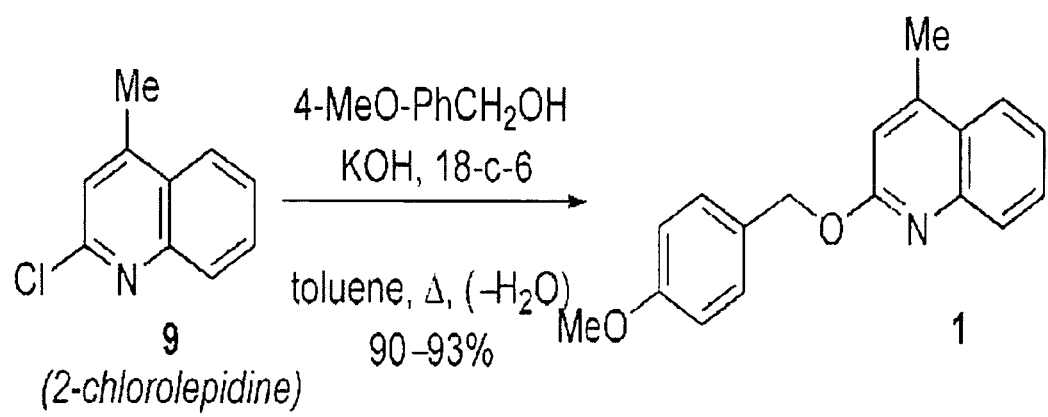
FIG. 2 depicts Equation (2) the preparation of 2-(4-methoxybenzyloxy)-4-methylquinoline, a lepidine ether according to compound 1 of the present invention.

PMB salt, compound 7 shown in FIG. 1, is reactive at room temperature in methylene chloride, but it is not soluble in the aromatic solvents such as trifluorotoluene or toluene, which we have found to be optimal for reaction efficiency. We therefore targeted a more hydrophobic reagent (i.e., lepidine salt, shown as compound 8 in FIG. 1) and prepared 2-(4-methoxybenzyloxy)-4-methylquinoline (compound 1 as shown in Equation 2 of FIG. 2)—see Note 1.

Preliminary experiments showed that lepidine derivative, compound 8, is soluble in aromatic solvents: addition of methyl triflate (MeOTf) to lepidine ether, compound 1, in trifluorotoluene[9] did not produce a visible precipitate despite rapid consumption of 1 with concomitant formation of polar material.[10] Lepidine ether 1 is significantly more stable than other PMB transfer reagents such as PMB chloride[3] and PMB trichloroacetimidate.[4] Furthermore, addition of methyl triflate to mixtures containing alcohols 2 and lepidine 1 affords PMB ethers 3, as shown in Table 1—see also Note 2.

Figure 3:
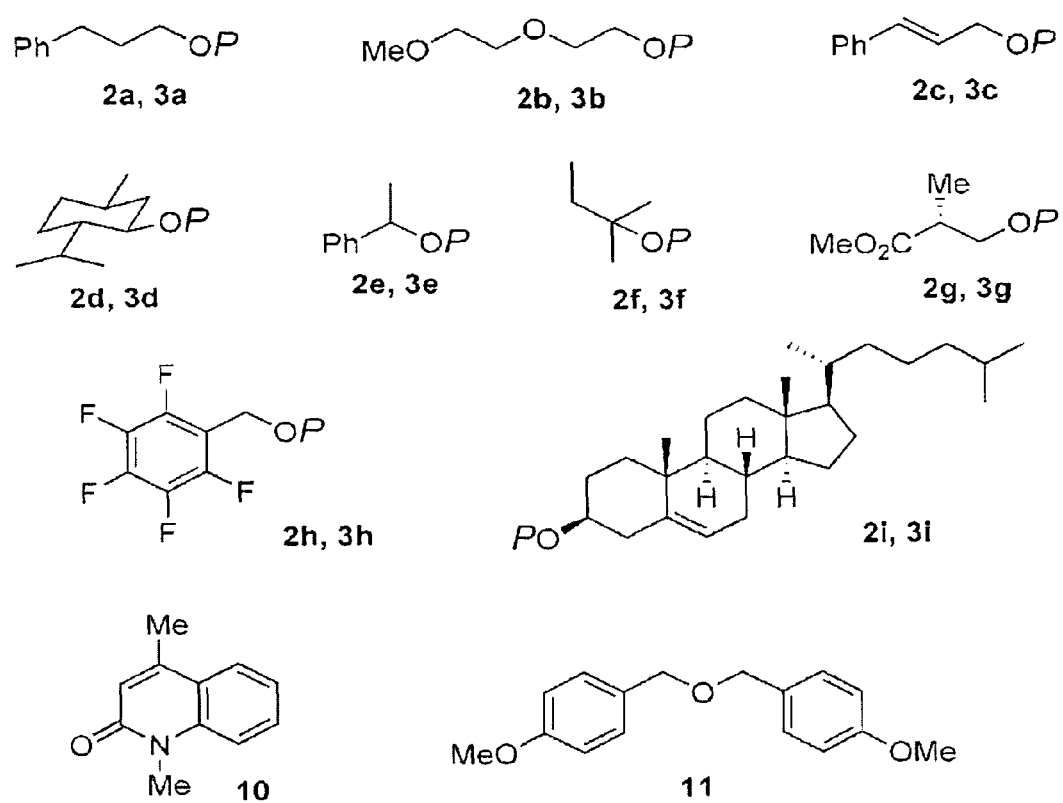
FIG. 3 shows the substrates and products from the arylmethylation reactions listed in Table 1 (for 2*a-i*, P=H; for 3*a-i*, P=PMB)
Figure 4:
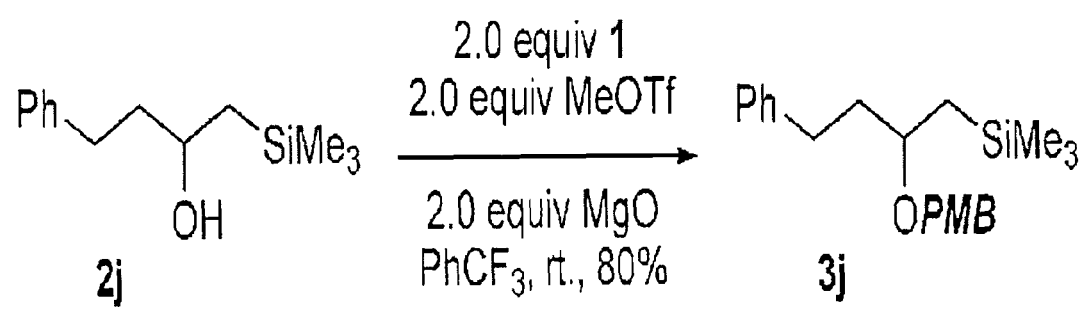
FIG. 4 illustrates Equation (3), the etherification of alcohol 2*j* according to an embodiment of the present invention.

As shown in Table 1, the formation of PMB ethers using compound 1 and methyl triflate occurs efficiently on a range of alcohols (depicted in FIG. 3). The optional presence of magnesium oxide (MgO) provides for higher yields and easier purification of compounds 3. N-Methyl-lepidone (compound 10, as shown in FIG. 3) is the expected by-product of this reaction; bis-PMB ether (compound 11), presumably derived from adventitious moisture and/or reaction with magnesium oxide, is also observed in varying amounts. Other aromatic solvents (e.g., toluene, as in entry 11) and heterogeneous acid scavengers (e.g., potassium carbonate, as in entry 6) may be employed in lieu of trifluorotoluene and magnesium oxide. Simple primary and secondary alcohols (entries 1-6) gave rise to the corresponding PMB ethers (3a-e) generally in good to excellent yield. Allylic alcohol 2c was not fully consumed for some reason (entry 3), whereas benzylic alcohols 2e and 2h proved to be good substrates (entries 5 and 9). Tertiary alcohols (e.g., 2f, entry 7) were less reactive. PMB-protection of cholesterol (2i-3i, entry 10) proceeded reasonably under the standard conditions (80%) despite limited solubility of 2i in trifluorotoluene. The same reaction in toluene afforded 3i in nearly quantitative yield (entry 11). The Roche ester (2g) gave rise to PMB ether 3g in 84% yield (entry 8). The etherification of alcohol 2j (shown in Equation 3) illustrates the tolerance of the reaction conditions to sensitive functionality. Alcohol 2j is subject to Peterson elimination[11] under acidic or basic conditions, but transfer of the PMB-group provides ether 3j with no evidence of the potential elimination by-product, 4-phenyl-1-butene.

In keeping with our earlier work on the synthesis of benzyl ethers,[6] and wishing not to be bound, we theorize that the current synthesis of PMB ethers

TABLE 1

Arylmethylation of representative alcohols (2 → 3, see FIG. 3)[a]

R—OH  2.0 equiv 1
2     2.0 equiv MeOTf  →  R—O—CH$_2$—C$_6$H$_4$—OMe
      2.0 equiv MgO                3
      PhCF$_3$, 0° C. to rt

| Entry | Alcohol 2 | Ether 3 | % yield[b] |
|---|---|---|---|
| 1 | 2a | 3a | 94 |
| 2 | 2b | 3b | 98 |
| 3 | 2c | 3c | 63[c] |
| 4 | 2d | 3d | 90 |
| 5 | 2e | 3e | 89 |
| 6 | 2e | 3e | 69[d] |
| 7 | 2f | 3f | 60[e] |
| 8 | 2g | 3g | 84 |
| 9 | 2h | 3h | 99 |
| 10 | 2i | 3i | 80[c] |
| 11 | 2i | 3i | 98[e] |

[a]Unless otherwise indicated, methyl triflate was added to a mixture of alcohol 2, lepidine 1, MgO, and trifluorotoluene under argon.
[b]Isolated yield.
[c]Alcohol 2 was not fully consumed after 1 h.
[d]Potassium carbonate (K2CO3) employed in lieu of MgO.
[e]Toluene employed in lieu of PhCF3.

proceeds by an SN1-type mechanism analogous to that observed from trichloroacetimidates. Important to the success of the present synthetic approach is that the neutral alcohol 2 does not react with methyl triflate, whereas alcohol 2 does react with the p-methoxybenzyl cation as it is released from active reagent compound 8.

Lepidine ether 1 provides several key advantages over PMB trichloroacetimidate: (1) ether 1 is more stable; (2) active reagent 8 is generated under non-acidic conditions; and (3) the by-product, lepidone 10, remains in solution until it is purged, either during aqueous workup, or on silica gel chromatography. In contrast, the acetamide by-product of trichloroacetimidate coupling reactions can cause problems during purification.

In summary, we have disclosed a new p-methoxybenzyloxy derivative of lepidine that, upon treatment with methyl triflate, transfers the PMB group to an awaiting alcohol substrate. Methylation of the lepidine core generates an activated reagent under effectively neutral conditions, allowing acid- and base-sensitive alcohols (e.g., 2j) to be protected as PMB ethers. We expect this invention to be of considerable utility.

Note 1: 2-(4-Methoxybenzyloxy)-4-methylquinoline (1) A mixture of 4-methoxybenzyl alcohol (3.6 g, 26 mmol), 2-chlorolepidine (3.6 g, 21 mmol), KOH (4.8 g, 86 mmol, ground with a mortar and pestle), toluene (41 mL) and 18-crown-6 (318 mg, 1.2 mmol) was heated at reflux for 1 h with azeotropic removal of water (Dean-Stark trap). The reaction mixture was then cooled to room temperature and partitioned between ethyl acetate (100 mL) and water (50 mL). The organics were washed (brine), dried (MgSO4), filtered, concentrated under vacuum, and purified on silica gel (elution with 5% EtOAc-hexanes) to provide 5.3 g of 1 (93% yield) as a white solid: $^1$H NMR (300 MHz, CDCl$_3$) δ 7.87 (br d, J=8.4 Hz, 2H), 7.62 (td, J=7.6, 1.3 Hz, 1H), 7.49-7.37 (m, 3H), 6.92 (d, J=6.7 Hz, 2H), 6.79 (s, 1H), 5.46 (s, 2H), 3.82 (s, 3H), 2.62 (s, 3H); $^{13}$C NMR (75 MHz, CDCl$_3$) δ 162.1, 159.7, 147.0, 146.8, 130.3, 129.8, 129.5, 128.0, 125.8, 124.0, 123.9, 114.1, 113.5, 67.4, 55.5, 18.9. IR 1611, 1573, 1514, 1470, 1448, 1396, 1329, 1303, 1246, 1174, 1130, 1039, 1020 cm$^{-1}$. HRMS (ESI$^+$) found 302.1163 (calcd for C$_{18}$H$_{17}$NO$_2$Na: 302.1157).

Note 2: Standard procedure for the arylmethylation of alcohols (2→3) An ice-cold mixture of 2-PMBO-lepidine 1 (200 mg, 0.72 mmol), benzotrifluoride (PhCF$_3$, 3.6 mL), MgO (29 mg, 0.72 mmol, vacuum-dried), and alcohol 2 (0.36 mmol) was treated dropwise with methyl triflate (82 μL, 0.72 mmol). The ice bath was removed, and the reaction mixture was stirred at room temperature for 30-60 min. until TLC analysis showed consumption of alcohol 2. The mixture was then diluted with ethyl acetate, decanted away from the MgO residue, washed (H2O), dried (MgSO4), filtered, concentrated at reduced pressure, and purified on silica gel to yield PMB ether 3 (see Table 1).

Accordingly, in the drawings and specification, there have been disclosed typical preferred embodiments of the invention, and although specific terms may have been employed, the terms are used in a descriptive sense only and not for purposes of limitation. The invention has been described in considerable detail with specific reference to these illustrated embodiments. It will be apparent to the skilled. however, that various modifications and changes can be made within the spirit and scope of the invention as described in the foregoing specification and as defined in the appended claims.

REFERENCES 1 (a) T. W. Greene and P. G. M. Wuts, *Protective Groups in Organic Synthesis*, John Wiley and Sons, New York, 3rd edn, 1999; (b) P. J. Kocienski, *Protecting Groups*, Thieme, Stuttgart, 3rd edn, 2003.

2 Y. Oikawa, T. Yoshioka and O. Yonemitsu, Tetrahedron Lett., 1982, 23, 885.

3 P. G. M. Wuts, p-Methoxybenzyl Chloride, in *Encyclopedia of Reagents for Organic Synthesis*, ed. L. A. Paquette, John Wiley and Sons, New York, 1995, Vol. 5, p. 3326.

4 (a) P. G. M. Wuts, 4-Methoxybenzyl 2,2,2-Trichloroacetimidate, in *Encyclopedia of Reagents for Organic Synthesis*, ed. L. A. Paquette, John Wiley and Sons, New York, 1995, Vol. 5, p. 3329; (b) Attractive method for the synthesis of PMB ethers using catalytic lanthanum triflate: A. N. Rai and A. Basu, *Tetrahedron Lett.*, 2003, 44, 2267.

5 *The Chemical Synthesis of Natural Products*, ed. K. Hale, CRC Press, Boca Raton, Fla., 2000.

6 (a) K. W. C. Poon and G. B. Dudley, *J. Org. Chem.*, 2006, 71, 3923; (b) K. W. C. Poon, S. E. House and G. B. Dudley, *Synlett,* 2005, 3142; (c) G. B. Dudley, U.S. patent application Ser. No. 11/399,300, 2006.

7 Benzyloxy salt 4 is commercially available from Sigma-Aldrich Chemical Co. (catalog # 679674-1g, 679674-5g).

8 Typical reagents for the formation of PMB ethers are more reactive and less stable than reagents for the synthesis of benzyl ethers; see P. J. Kocienski, *Protecting Groups*, Thieme, Stuttgart, 3rd edn, 2003, p. 257.

9 Trifluorotoluene, also known as benzotrifluoride or BTF, is often used industrially as an alternative to dichloromethane.

10 An analogous modification of Mukaiyama's reagent improved its solubility in non-polar solvents; see: S. H. Oh, G. S. Cortez and D. Romo, *J. Org. Chem.,* 2005, 70, 2835.

11 D. J. Ager, *Org. React.,* 1990, 38, 1.

That which is claimed:

1. A para-Methoxybenzyl ether having the formula of compound 1

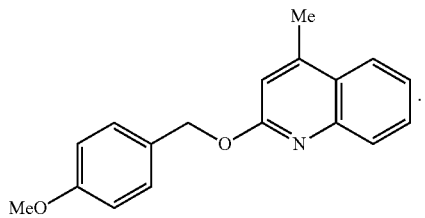

* * * * *